(12) United States Patent
Lichy et al.

(10) Patent No.: US 12,322,097 B2
(45) Date of Patent: Jun. 3, 2025

(54) COMPUTER-IMPLEMENTED METHOD FOR EVALUATING AN ANGIOGRAPHIC COMPUTED TOMOGRAPHY DATASET, EVALUATION DEVICE, COMPUTER PROGRAM AND ELECTRONICALLY READABLE DATA MEDIUM

(71) Applicant: Siemens Healthineers AG, Forchheim (DE)

(72) Inventors: Matthias Lichy, Nuremberg (DE); Bernd Hofmann, Erlangen (DE); Bernhard Schmidt, Fuerth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 425 days.

(21) Appl. No.: 17/868,926

(22) Filed: Jul. 20, 2022

(65) Prior Publication Data
US 2023/0028300 A1   Jan. 26, 2023

(30) Foreign Application Priority Data
Jul. 23, 2021   (DE) .................... 10 2021 207 957.1

(51) Int. Cl.
*G06T 7/00* (2017.01)
*A61B 6/50* (2024.01)
*G06T 7/11* (2017.01)

(52) U.S. Cl.
CPC ............ *G06T 7/0012* (2013.01); *A61B 6/507* (2013.01); *G06T 7/11* (2017.01); *G06T 2207/10081* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 2015/0010225 A1 | 1/2015 | Popovic et al. | |
| 2016/0287093 A1 | 10/2016 | Choi et al. | |
| 2017/0287132 A1 | 10/2017 | Ertel et al. | |
| 2018/0032653 A1 | 2/2018 | Aben et al. | |
| 2018/0174490 A1* | 6/2018 | Randles | G09B 23/303 |
| 2020/0305816 A1 | 10/2020 | Lichy et al. | |
| 2022/0093267 A1 | 3/2022 | Laksari et al. | |

FOREIGN PATENT DOCUMENTS

| | | |
|---|---|---|
| DE | 102016205507 A1 | 10/2017 |
| WO | WO 2020154398 A1 | 7/2020 |

* cited by examiner

*Primary Examiner* — Leon Flores
(74) *Attorney, Agent, or Firm* — Harness, Dickey & Pierce, P.L.C.

(57) ABSTRACT

At least one vascular tree supplying at least a part of the hollow organ in the computed tomography dataset is segmented, and a tree structure up to an order possible based on the blood vessel segmentation result is determined from a blood vessel segmentation result. Perfusion information for each edge in the tree structure is assigned as at least one of the computed tomography data assigned to the blood vessel segment or at least one value derived therefrom. Adjacent hollow organ segments of the hollow organ are defined based on supply by adjacent blood vessels in the tree structure, and the tree structure and the perfusion information are analyzed to determine hemodynamic information to assign to hollow organ segments. At least a part of the hemodynamic information in at least one of the computed tomography dataset or a visualization dataset derived therefrom is then visualized.

25 Claims, 8 Drawing Sheets

COMPUTER-IMPLEMENTED METHOD FOR EVALUATING AN ANGIOGRAPHIC COMPUTED TOMOGRAPHY DATASET, EVALUATION DEVICE, COMPUTER PROGRAM AND ELECTRONICALLY READABLE DATA MEDIUM

CROSS-REFERENCE TO RELATED APPLICATION(S)

The present application claims priority under 35 U.S.C. § 119 to German Patent Application No. 10 2021 207 957.1, filed Jul. 23, 2021, the entire contents of which are incorporated herein by reference.

FIELD

One or more example embodiments of the present invention relate to a computer-implemented method for evaluating an angiographic three-dimensional computed tomography dataset of an acquisition region comprising a hollow organ, in particular the intestine, of a patient. One or more example embodiments of the present invention additionally relate to an evaluation device, a computer program and an electronically readable data medium.

BACKGROUND

Computed tomography is an established imaging modality for medical, in particular clinical applications. The process entails moving an X-ray source around a patient along a scanning trajectory in order to acquire in particular two-dimensional projection images of an acquisition region using different projection geometries, in particular different projection angles. From the set of in particular two-dimensional projection images, a three-dimensional computed tomography image dataset can be reconstructed, for example by filtered backprojection.

Angiography is a special variant of X-ray imaging. The procedure involves administering a contrast agent, for example a contrast agent containing iodine, to the patient in order to make the blood vessels in the acquisition region as clearly visible as possible. Whereas coronary imaging, for example, in which images of the heart and the coronary vessels can be acquired, is generally known, angiographic examinations are also performed for a great many other organs, in particular hollow organs, in order to enable hyperperfused and/or hypoperfused regions to be identified. Angiographic imaging of the intestine is a particularly common example in this context. In this regard, the accurate detection and attribution both of pathologies of the blood vessels and of their associated intestinal segments constitutes an important question in the imaging of the abdomen, both in terms of the diagnosis and in planning and carrying out the therapy. In cases of segmental ischemia of the intestine, for example, it is important to ensure accurate tracing and detection of the affected blood vessel segments. In another example, where intestinal resections have already been carried out, changes in the perfusion of the remaining intestinal segments may occur, which can have an impact on the significance of hyperemic segments that are to be observed in a static singular phase. In the extreme case, following intestinal transplantation for example, changes in the perfusion of intestinal segments can result due to changes in blood flow, pathological processes of the intestinal wall, changes to and/or narrowing of the blood vessels, and combinations thereof. Changes in the vascular tree in this case also include collateralization, in which efferent and afferent blood vessels are considered. For the intestine and all other hollow organs conceivable in this regard, precise discrimination and assignment of the genesis is the essential basic prerequisite for any therapy planning, implementation and monitoring.

SUMMARY

In a computed tomography examination of hollow organs, it is well-known in the prior art to employ traditional axial, coronary and/or sagittal computed tomography methods for visualizing the vascular anatomy and the hollow organ segments. These, however, provide only a rough indication in terms of the localization of a pathology. An assessment of perfusion parameters, in particular level-of-perfusion parameters or hemodynamic parameters generally, is currently carried out only visually by a person making a diagnosis, for example a radiologist. This often results in a second manual and visual exploration of the entire hollow organ needing to be performed intraoperatively by a person conducting an intervention. In this case, however, smaller blood vessel segments cannot be identified sufficiently clearly, for example in the case of accumulation in the fatty tissue of the omentum majus, and any blood vessel thromboses that may be present can only be detected manually in a less reliable way by feel.

There therefore exist in the prior art a great many application areas in which more accurate information would be desirable. In the example of the intestine as a hollow organ, as exact a localization of the affected intestinal segments as possible is desirable in the case of inflammatory intestinal diseases so that as little healthy tissue as possible needs to be removed. This also includes the evaluation of possible anastomoses and collaterals. In the case of intestinal transplantations, visualizing options for anastomosis is of relevance. Furthermore, the monitoring of the blood vessel and intestinal anastomoses with regard to an insufficiency is important in this context. As regards tumor resections, in particular of the small intestine, it is desirable to detect variations in the anatomy and blood circulation with certainty. In some applications it is necessary to evaluate both the arterial and the portal venous branch in this case.

In known applications in respect of the intestine, assigning the vascular anatomy visualized in the computed tomography imaging to the supplied intestinal areas is rendered difficult due to the compact invagination, displacement and motility of the intestine. Due to this variability with respect to time, the correlation and orientation by way of fixed landmarks in the imaging is essential for faster and better identifiability and detectability of intestinal pathologies. This is made even more difficult due to the fact that a change in the positional relationships results during the operative cut-down. This effect is independent of the type of operative exploration, for example open surgical as opposed to laparoscopic/robot-assisted interventions.

At least one object underlying example embodiments of the present invention is therefore to disclose an automated evaluation mechanism or device for angiographic computed tomography image datasets of a hollow organ which is improved by comparison with the prior art and which permits in particular an improved spatial assignment of the results.

In order to achieve this object, a computer-implemented method, an evaluation device, a computer program and an electronically readable data medium.

An inventive computer-implemented method for evaluating an angiographic three-dimensional computed tomography dataset of an acquisition region comprising a hollow organ, in particular the intestine, of a patient, wherein at least one piece of spatially resolved hemodynamic information in respect of the hollow organ is determined, comprises the following steps:

provided the computed tomography image dataset, segmenting at least one vascular tree supplying at least a part of the hollow organ in the computed tomography dataset, determining a two-dimensionally representable tree structure from the blood vessel segmentation result up to an order possible on the basis of the blood vessel segmentation result, wherein branches of blood vessels form nodes and blood vessel segments of an order form edges, assigning perfusion information for each edge in the tree structure as the computed tomography data assigned to the blood vessel segment and/or at least one value derived therefrom, defining adjacent hollow organ segments of the hollow organ based on the supply via adjacent blood vessels in the tree structure, analyzing the tree structure and the perfusion information for paths from a root of the tree structure to an end edge and/or for all edges of an order in order to determine the hemodynamic information that is assignable to hollow organ segments, visualizing at least a part of the hemodynamic information in the computed tomography dataset and/or a visualization dataset derived therefrom.

Since the method serves for evaluating an angiographic computed tomography dataset, the latter is first provided, be it by the acquisition of images via the computed tomography device, which preferably can itself be embodied for performing the evaluation just described, or else from a storage location, for example a picture archiving system (PACS). The computed tomography dataset is a three-dimensional computed tomography dataset which has been reconstructed, as is generally known, from two-dimensional projection images and which, as will be explored in greater detail below, may also contain different partial image datasets.

It is now proposed not to conduct the analysis starting from the hollow organ and/or manually, as is the conventional practice, but to use the clearly recognizable representation of the blood vessels and their regular structure in order also to establish the spatial assignment via these. To that end, it is proposed in practice initially to segment at least a part of the vascular tree supplying the hollow organ in the computed tomography dataset. Because a contrast agent has been used, the blood vessels are identifiable with exceptional clarity, thus enabling segmentation algorithms known in the prior art to be used, in particular also the multiplicity of approaches specifically geared to vascular systems proposed in particular for coronary angiographic applications.

Thereafter, a two-dimensionally representable tree structure is determined from the blood vessel segmentation result up to an order possible on the basis of the blood vessel segmentation result, wherein branches form nodes and blood vessel segments of an order form edges (boughs). In other words, generally known techniques such as blood vessel segmentation, blood vessel unfolding and blood vessel tracing are resorted to in order to obtain a two-dimensionally representable tree structure. This may be understood as a blood vessel spreading together with a blood vessel unfolding. The root may in this case be a blood vessel selectable for example on the basis of a user specification, in the case of the intestine, in particular the small intestine, for example a mesenteric artery. After each branch, in particular bifurcation, where the branch in the tree structure is to be seen as a node, further blood vessel segments follow, as it were as "boughs" of the next-higher order.

Each edge in said tree structure, i.e. each blood vessel segment, is then assigned perfusion information from the computed tomography data. Basically, the computed tomography data of the blood vessel segment according to the blood vessel segmentation itself can of course be referred to in this process, though it is preferred to reduce the data volume already at this point and set a limit to at least one value representative of the blood flow, wherein for example a statistical summary of the computed tomography data assigned to the blood vessel segment can be carried out. For example, a mean value, a median, a variance and the like can be determined for each partial image dataset in the computed tomography dataset. In another embodiment, it is also possible to retain just the computed tomography data along a vessel centerline that is derivable from the blood vessel segmentation result or the like. Determining a value in this way may be understood as a "measurement". In this sense, therefore, a projection and possibly a compression of the computed tomography data into the notional possible two-dimensional visualization plane of the tree structure is carried out.

It should be noted at this point that ultimately the spatial resolution determines up to which order blood vessels of the vascular tree can be resolved. For example, it is conceivable to segment up to the fourth or fifth order.

In the following, use is now made of the fact that the blood supply of the hollow organ, in particular the intestine, has been recognized as extremely regular. If, in the presentation, the hollow organ, in practice in particular the small intestine, together with the blood vessels supplying it, were "extracted" and placed flatly linearly in a visualization plane, an extremely regular tree structure of the supply would be recognized. This line of thought is now used in order to subdivide the hollow organ into segments which are supplied by the blood vessel segments assigned to the end edges. Furthermore, however, this insight also permits blood vessel segments to be detected which are entirely missing due to deviations from the assumed regularity of the tree structure, and which therefore are no longer supplied sufficiently with blood, by reason that the contrast agent can be identified clearly enough, which subject will be dealt with in greater detail below.

To put it another way, since the portion of the blood vessel system under consideration serves to supply the hollow organ, it is now possible to define adjacent hollow organ segments of the hollow organ on the basis of the supply via adjacent blood vessels in the tree structure. This may be understood as a spreading and an unfolding of the intestine in respect of the notional visualization plane of the tree structure. The hollow organ can therefore be modeled as extending along the end edges of the tree structure.

This means that in the access proposed according to one or more example embodiments of the present invention, the hollow organ is localized and subdivided in respect of the blood supply on the basis of the blood vessel segmentation result. Thus, a novel application of organ and blood vessel unfolding is provided. The approach described here is vastly superior to other ways of proceeding that operate on the basis of a segmentation of the hollow organ or of the centerline of the hollow organ that is to be performed largely manually, and is more tailored to the clinical issue.

Particularly advantageously, information about the vascular system and its assignment to the supplying of the hollow organ and to the hollow organ itself is present in an easy-to-handle data structure which can subsequently be evaluated, i.e. analyzed, automatically in order to determine the hemodynamic information, for example as level-of-perfusion information. In this process, for example, paths from a root of the tree structure to an end edge can be considered; however, it is also possible in addition or alternatively to conduct analyses as it were in the transverse direction, i.e. within an order. An analysis of the tree structure can provide pointers to blood vessel segments missing overall. Since it is known to which hollow organ segment which end edge and therefore each blood vessel segment is assigned, in relation to which, moreover, the spatial location is also known on account of the blood vessel segmentation result, it is now possible to visualize at least a part of the hemodynamic information, either in the computed tomography dataset itself and/or in a visualization dataset derived therefrom, in which case such a derivation certainly also comprises, for example, visualizing the tree structure in the visualization plane.

Particular advantages arise in the method according to one or more example embodiments of the present invention as regards the small intestine as a hollow organ since successful automatic segmentation approaches often failed in that respect until now or only deliver incomplete or incorrect results. Here, for the first time, the method according to one or more example embodiments of the present invention offers an approach for providing automatic support for diagnostic findings in the localization of ischemias (and other phenomena) since it is not the intestine but its supply which is considered in order to find and also to localize deviating regions in at least one small intestine segment. Even if the intestine, in particular the small intestine, will frequently be referred to as an example of the hollow organ within the scope of this description, preferably for localizing ischemias, applications with regard to other hollow organs with similar issues and problems are of course also conceivable. For example, the procedure described here can also be applied to computed tomography datasets showing the stomach and/or the esophagus. Such a segment-by-segment supply is given in respect of the spinal cord also, such that the procedure described here can be applied. Another possible application example in this regard is the detection of ischemia, as occurs for example in the case of the spinal cross-section.

In a particularly advantageous embodiment of the present invention, it can be provided that in the case of a computed tomography dataset acquired using multi-energy imaging for segmentation of the vascular tree and/or for determining at least a part of the perfusion information, a contrast agent dataset obtained by material decomposition is used. Multi-energy imaging is already well-known in the prior art and relates to the presence of computed tomography data assigned to different energy spectra. In this connection, a photon-counting X-ray detector can particularly advantageously be used for the acquisition of the projection data on which the computed tomography dataset is based, which photon-counting X-ray detector enables the energies of individual photons to be measured and sorted accordingly, for example into so-called energy bins, such that partial image datasets assigned to different X-ray spectra or energy intervals can be contained in the computed tomography dataset. Techniques such as material decomposition permit in particular image datasets assigned to specific materials to be determined, in particular also quantitatively. Accordingly, a particularly advantageous embodiment of the present invention can provide that at least one contrast agent dataset, in particular an iodine dataset, is determined which shows only the fractions of the contrast agent. This not only enables an improved segmentation of the vascular tree and an improved determination of the perfusion information, but additionally also an improved overall determination since the amount of contrast agent, in particular iodine, in a blood vessel segment represents a direct measure for the perfusion. Particularly advantageously, the perfusion information may therefore comprise quantitative contrast agent concentrations from the contrast agent dataset.

In a particularly advantageous embodiment of the present invention, it can be provided, as already indicated, that blood vessel segments not detected during the blood vessel segmentation are determined by evaluation of the tree structure in that a regularity of the tree structure is assumed, for example bifurcations in each case up to a predefined, in particular the highest, order, deviations from the regularity being determined as indicating missing blood vessel segments. Use is therefore made of the recognized regularity and uniformity of the blood supply, at least in respect of the order of blood vessel segments that can be considered here, in order to identify portions of the tree structure in which blood vessel segments are missing but which should be present based on the assumed regularity. In this way, missing portions beginning at least in lower-order blood vessel segments can particularly advantageously be determined since these exert the strongest influence on the health of the patient, by comparison with individual "omitted" higher-order blood vessel segments. In this case the simplicity of the data structure can once again be exploited algorithmically since only a tree structure comprising nodes and edges needs to be checked for deviations from regularity. Further identified deviations, for example trifurcations or the like, can be assigned to the tree structure as supplementary information. It should be noted that already such a determination of missing blood vessel segments can lead directly to a piece of hemodynamic information since at least hypoperfusion, in particular ischemia, is clearly present in the correspondingly definable hollow organ segments.

In practice it can be provided that the missing blood vessel segments of the tree structure determined by the evaluation of the tree structure are added on the basis of the location in the tree structure, in particular with perfusion information indicating no flow, and/or that for an evaluation region in the computed tomography dataset a new blood vessel segmentation process, in particular using a changed parameterization, is performed in order to find the determined missing blood vessel segments. As well as a simple addition with perfusion information indicating an absent blood flow, an attempt can also be made to use the knowledge that blood vessel segments ought to be there in order to initiate a further attempt at their segmentation in the computed tomography data, in particular a contrast agent dataset. If successful, perfusion information can also be derived from the computed tomography data.

It should also be noted that, of course, when adding blood vessel segments not yet included in the blood vessel segmentation result to the tree structure, an adding and corresponding classifying definition of at least one hollow organ segment supplied by the corresponding end edges is carried out.

In a further particularly advantageous embodiment of the present invention, it can be provided that organ portions in the computed tomography dataset are assigned to hollow organ segments defined on the basis of the tree structure on the basis of the positional information of the blood vessel segments of the end edges known from the blood vessel segmentation result. In this case, therefore, the tracing of the blood vessels is used in order also to find specifically the location of the associated hollow organ portions. Whereas it would be conceivable in principle, should such a sufficiently robust method be available, to perform this on the basis of a hollow organ segmentation result so that only actual hollow organ computed tomography data is selected, such is, however, also conceivable without the use of such a method. Locally usable segmentation approaches for hollow organs, in particular the small intestine, also comprise the use of the knowledge about a surrounding fatty layer which can be found in the computed tomography dataset and consequently can enable a segmentation of the hollow organ, at least locally. An in particular local segmentation of the hollow organ can of course also use other approaches and/or also take supplementary information into consideration, for example additional computed tomography data specifically acquired for this purpose or even information of a preliminary dataset registered with the computed tomography dataset. In an exemplary embodiment, a dual-contrast method can be used.

In practice it can be provided that the organ portions are specified on the basis of a predefined environment and/or an environment determined on the basis of positional information of adjacent blood vessel segments and/or on the basis of an, in particular local, segmentation of the hollow organ. Various approaches can be chosen for assigning organ portions to hollow organ segments, i.e. for determining (or estimating) the actual location and extent of the thus far abstractly defined hollow organ segments. For example, certain predefined environments of the blood vessel segment corresponding to the end edge can be assigned as organ portion to the corresponding hollow organ segment. Generally speaking, it is above all the tissue limiting or ultimately forming the hollow organ that is of the greatest interest since for this also, as will be disclosed later, perfusion information can be determined, so that for example a local segmentation or at least an exclusion of certain computed tomography data can take place. Another approach for allocating organ portions in the computed tomography dataset to hollow organ segments defined on the basis of the tree structure can carry out the assignment for example such that the midpoint between blood vessel segments assigned to the respective end edges is determined and called upon as the limit or part of the limit.

An additional determination of hollow organ portions also in the computed tomography dataset, in particular with an at least local segmentation, is advantageous in many respects. Thus, it is possible initially also to include the hollow organ in a visualization based on the computed tomography dataset. It can thus be provided that the hollow organ and/or the organ portions are highlighted at least partially in the visualization, in particular in addition to blood vessel segments.

Particularly advantageously, however, perfusion information can equally be determined from the computed tomography data of the organ portion for each hollow organ segment assigned to an end edge and said perfusion information can be inserted into the tree structure, in particular by fusion or as supplementary information and/or assigned to the respective end edge.

It can also be provided in this context, in particular in addition or alternatively to an analysis of the tree structure, that blood vessel segments not detected in the blood vessel segmentation are determined by evaluation of the assignment result of organ portions to hollow organ segments, in particular on the basis of unsupplied or inadequately supplied organ portions of a hollow organ segmentation result and/or unassigned or wrongly assigned sections of the computed tomography dataset. If environments of a certain size are assigned as organ portion to the hollow organ segments (and therefore supplying blood vessel segments) or if a maximum size is predefined for an organ portion, organ portions not assigned to a hollow organ segment may also remain in the computed tomography dataset. If these are large, it is to be assumed that a non-supply or inadequate supply is present here, for example a blood vessel segment of the highest order or even of lower orders is no longer supplied with blood, so that they are not visible in the computed tomography dataset and consequently cannot be segmented. Such portions that cannot be reliably assigned can also be inferred when for example limits are defined centrally between blood vessel segments assigned to end edges, when for example clearly overlarge organ portions occur. Such a detection of unsupplied or inadequately supplied organ portions can also be inferred on the basis of the distances between blood vessel segments assigned to nearest-neighbor end edges, in particular in the case of at least local hollow organ segmentation along its course. Clearly, a great many actual possibilities are conceivable for detecting an absent or much too low blood supply on the basis of the assignment to hollow organ segments and consequently to supplying blood vessel segments.

As has already been indicated, it is also particularly preferred in the context of an assignment of organ portions to hollow organ segments if perfusion information is also determined from the computed tomography data for each hollow organ segment assigned to an end edge and said perfusion information is inserted into the tree structure, in particular by fusion or as supplementary information and/or assigned to the respective end edge. Even if individual blood vessel segments may no longer be identifiable, it is nevertheless entirely possible, in particular within the scope of multi-energy imaging and a contrast agent quantification, to detect contrast agent fractions in the perfused tissue and to draw a corresponding conclusion as to how the tissue is supplied by the blood vessel segment assigned to the end edge. If, for example, a quantitative contrast agent dataset is available, a static handling of contrast agent amounts in the organ portion assigned to the hollow organ segment can take place, for example a summation, an averaging and the like. The perfusion information correspondingly comprising at least one statistically derived value can be stored in addition to the perfusion information of the end edge assigned to the latter or else also fused to form common perfusion information. Said perfusion information related to the hollow organ segment is then of course also taken into account in the analysis for determining the hemodynamic information. In this connection, an at least local segmentation of the hollow organ is extremely useful in order also to be able to consider only its perfused tissue.

A particularly advantageous embodiment of the present invention provides that collaterals and/or anastomoses detected during the determination of the tree structure and/or in the analysis of the perfusion information are removed from the tree structure and stored together with their attachment points as supplementary information to the tree structure, the supplementary information being taken into account in the determination of the hemodynamic information and/or in the visualization. In particular, collaterals can occur in a blood vessel system which represent, as it were, a cross-connection between two blood vessel segments of the same or a different order and can be detected already in the blood vessel segmentation result by way of corresponding algorithms or logic processes. However, as will be explained in more detail below, collateralization can still be evident or possibly be confirmed also in the analysis of the flow information. In other words, detected collaterals and/or anastomoses can be made plausible against one another in the blood vessel segmentation result and the analysis. Since such supplementary blood vessels lead to a divergence from the wanted tree structure (branching with unique paths without the possibility of forming circles or exiting a region of interest under consideration), they can be extracted from the tree structure and stored as supplementary information. If, for example, the existence of a collateral is already known from the blood vessel segmentation result and if the corresponding supplementary information relating to the tree structure is available, an increase in the blood flow rate discovered during the analysis of the perfusion information, for example, can be explained by this. In particular, it is therefore also conceivable that the presence of a collateral and/or anastomoses can also be deduced from the "disappearance" or "addition" of blood flow at a branch, for example if more blood comes from the afferent vessel segment than flows through the efferent vessel segments. Collaterals in the vascular tree, for example, can also be specially highlighted or indicated within the scope of the visualization.

In beneficial exemplary embodiments, as already mentioned, the computed tomography dataset can comprise a time series of three-dimensional computed tomography images which can reveal, for example, the contrast agent uptake, the contrast agent present (fill phase) and/or the contrast agent outflow. In particular, projection image sets can be acquired extremely quickly using current computed tomography devices, from which projection images a reconstruction is possible such that multiple computed tomography images exist which show the fill phase in respect of the contrast agent. In such a context it can be beneficial to determine time-averaged perfusion information. It is preferable, however, if in addition or alternatively the perfusion information comprising at least one time variation curve is determined. Contrast agent curves of said type which can then result are already generally known in the prior art and can already contain information as to whether the perfusion is normal or perhaps disrupted. For example, a contrast agent curve can extend in width and length with regard to a disrupted flow. Suchlike can then be taken into account accordingly during the analysis.

While it may be sufficient in simple exemplary embodiments of the present invention to mark blood vessel segments exhibiting too low a flow rate according to the flow rate information and/or the assigned hollow organ segments as hemodynamic information for supporting the detection, for example, of hollow organ segments affected by an ischemia, the present invention, however, also permits much more accurate evaluations.

In a particularly preferred embodiment of the present invention, it can be provided that for the analysis of the perfusion information for at least one order, in particular at least one highest order, a first perfusion information curve over all blood vessel segments of the order, i.e. all edges of the order, is determined and analyzed, in particular statistically, in order to determine the hemodynamic information. This is an example of an analysis for all edges of an order. Basically, it is to be assumed as a starting point that at least substantially like or comparable blood flow properties are present over all the blood vessel segments of an order, which should be reflected in the flow information assigned to the edges of the order. Possibly there may also already be information available indicating what is to be expected in blood vessel segments of the corresponding order, so that a comparison with external values can also take place. In practice it can be provided for example that in the case of a deviation fulfilling a relevance criterion of a piece of perfusion information from a plurality of perfusion information of the first perfusion information curve or a predefined, order-specific comparison value in the blood vessel segment, a hyperperfusion is determined in the case of upward deviations, and a hypoperfusion in the case of downward deviations. If, for example, in the case of all blood vessel segments of an order except for one, a value of the perfusion information indicating the perfusion lies within a certain interval, yet for a blood vessel segment outside of said interval a hyperperfusion is assumed (if the value lies above) or a hypoperfusion (if the value lies below), wherein such occurrences can of course also apply to multiple blood vessel segments of an order. In other words, "transverse gradients" of the perfusion information can therefore occur in the tree structure, which may point to divergent perfusion properties.

It is also particularly advantageous in this context if, in particular in addition to the first perfusion information curves, for at least a part of the paths from a root of the tree structure to an end edge, a second perfusion information curve over all the blood vessel segments of the path is determined and analyzed in order to determine the hemodynamic information, in particular with regard to the gradient. In particular, therefore, for each end edge for which there is precisely one path in the tree structure on account of the construction (in the case of the above-described exception handling of collateralizations), a second perfusion information curve to this path can be determined. In other words, the second perfusion information curve is therefore determined in the perfusion direction or counter thereto, which means both an anterograde and a retrograde procedure are possible. It is in particular possible and beneficial to analyze the gradients along said second flow information curves since these ultimately describe perfusion properties. In an actual embodiment it is therefore possible to determine along the vascular tree, described by the tree structure, for example a gradient of signal intensity values or, preferably in multi-energy imaging, of the contrast agent concentration in order to determine from this directly perfusion properties as well as flow/flow reserve properties. Useful hemodynamic information can also be determined directly by comparison of the different second perfusion information curves for the different end edges.

Thus, it can be provided in practice that the analysis is conducted by comparison of second perfusion information curves assigned to different paths, in particular statistical comparison, and/or by comparisons with at least one reference value for at least one gradient, in order to determine a hyperperfusion and/or a hypoperfusion. It also applies to the second perfusion information curves that these should extend over the orders at least substantially comparably or identically, wherein deviations may point to a hypoperfusion or hyperperfusion. In this case a statistical analysis can be conducted for example for all second perfusion information curves, at least with regard to higher-order gradients. Alternatively or in addition, the comparison with external reference values is also conceivable. With regard to the second perfusion information curves, it can furthermore also be provided that a collateral and/or an anastomosis is indicated in the event of a positive gradient in the peripheral direction. This is because normally the blood volume should not increase compared to a lower-order vessel which feeds the higher-order blood vessel segment. An atypical second perfusion information curve, which can refer for example to the contrast agent concentration as a value derived from the computed tomography data, can therefore exhibit an initial rise for example in the central-to-peripheral direction, i.e. a positive gradient, where a collateral flows in and supplies further blood, and/or, at another node, reveal a clearly excessively strong decline, i.e. a high negative gradient, where for example a higher-order blood vessel segment is inadequately supplied. Both the influence of collaterals, for example with regard to a hyperperfusion, and a presence of a hypoperfusion can therefore be determined via a stochastic analysis, for example.

Generally speaking, it can be provided within the scope of the analysis that at least one hemodynamic parameter is determined as hemodynamic information, in particular from the second information curves. In practice it can be provided for example that a surrogate parameter for the perfusion and/or the blood flow and/or the blood flow reserve, in particular the FFR (Fractional Flow Reserve), is determined as the hemodynamic parameter, in particular taking into account a vessel diameter that is derivable from the blood vessel segmentation result and/or the influence of collaterals and/or anastomoses. For example, the surrogate parameter for the perfusion and/or the blood flow and/or the blood flow reserve can be calculated on the basis of a gradient of the respective second perfusion information curves, based on morphological information or the contrast agent concentration, taking into account the change in cross-section of the blood vessel (correction due to partial volumes).

Within the scope of the analysis of the blood flow information, it may also be particularly advantageous if a correlation value describing the common blood supply is determined for at least one pair of paths from a root of the tree structure to an end edge, in particular taking into account collaterals and anastomoses, wherein the at least one correlation value is used for the assignment of comparable hemodynamic behaviors to common behavioral regions. In other words, the correlation value, which can be expressed for example as a probability value, can describe the correlation between the paths, which on the one hand can relate to the spatial proximity which can be defined by way of the common portions of the path (up to which order), wherein relationships can however also arise or be reduced due to the presence of collaterals and/or anastomoses. For example, a common cause of a hyperperfusion may also be based in a spatially apparently more remote path in which a collateral flowing into the other path originates, which therefore can then also establish a hypoperfusion in the path occurring on account of the collateral carrying away blood. Such correlation values can therefore help in this case to distinguish which hemodynamic properties might belong to which local phenomenon and which are possibly to be assigned even to a systemic phenomenon.

With regard to the visualization, as has already been indicated, various advantageous embodiments are conceivable, wherein both visualizations on the basis of the computed tomography dataset are conceivable as well as visualizations on the basis of intermediate results, such as, for example, the tree structure with assigned hollow organ segments or on the basis of visualization options derived from the computed tomography dataset. In practice it can be provided for example that a cinematic vessel representation is realized for the visualization, for example in the manner of an overflight, and/or an overlay representation of hemodynamic information, in particular an overlay of computed tomography data, and/or a highlighting of hollow organ segments and/or blood vessel segments resulting as a function of hemodynamic information. In an example, a curved MPR (multiplanar reconstruction) along at least one vessel centerline determined from the blood vessel segmentation result can be determined as a visualization dataset. Rendered representations which relate only to a part of the hollow organ and/or a part of the vascular tree are also realizable and conceivable on the basis of the segmentation and analysis results, wherein further information, for example hemodynamic information, can then likewise be integrated into such visualization datasets.

In this connection it may also be particularly beneficial if at least one anatomical landmark is detected in the computed tomography dataset and also visualized and/or placed in spatial relationship with at least one blood vessel segment and/or hollow organ segment. In this case anatomical landmarks may of course also be branches of blood vessels which can be discovered anyway within the scope of the segmentation of the vascular tree and the vessel tracing. However, other clearly visible landmarks, which particularly advantageously may also be recognizable in reality, for example during a medical intervention, are also detectable. Landmarks are useful not just for orientation, for example during the visualization, but can also be useful with regard to medical interventions, be they surgical or minimally invasive, since they permit guidance. If, for example, an ischemic region is detected and localized via the herein-described evaluation of the computed tomography dataset, changes can still occur up to the time of a medical intervention due to the movement of the hollow organ, in particular in the case of the intestine, which changes can also affect landmarks, which then permit an improved localization during the medical intervention.

Generally, or at least for substeps of the method described here, it is of course also possible to set a limit to a region of interest (ROI) defined in particular by a user. This can be beneficial for example when it is already roughly known in which region an anomaly that is to be detected is likely to lie. As a result of the visualization—as also generally in the method according to one or more example embodiments of the present invention—the hemodynamics can then also be detectable and represented for a user in such a way that the latter is able to draw conclusions, for example in relation to pathologies or the like, and/or undertake therapy planning. In other words, this furthermore means that the method described here is aimed at providing information relating to the hemodynamics, in particular with regard to the perfusion, which plays a useful and supporting role in a diagnosis that is to be conducted and/or in therapy planning, but is not or cannot replace a diagnosis that is to be reached and/or therapy planning that is to be carried out by a human operator, in particular a physician.

Particularly advantageously, a further automated evaluation with regard to issues, physical quantities, phenomena and effects in the acquisition region can of course also be carried out on the basis of the hemodynamic information. Thus, it is possible for example, via the hemodynamic information, to provide multiparametric maps with regard to the vascular tree and/or the hollow organ, for example surrogate parameters for perfusion, blood flow and blood flow reserve, which can be submitted for a further data analysis, for example with regard to the FFR. In other words, further evaluations and reconstructions can be carried out based on the hemodynamic information.

In addition to the method, the present invention also relates to an evaluation device, in particular in a or as a computed tomography device, having a control device embodied to perform the inventive method. All statements made in relation to the inventive method apply analogously to the inventive evaluation device, so that the already cited advantages can also be obtained with said device. In particular, therefore, a computed tomography device is also conceivable as an evaluation device, wherein the control device of the computed tomography device can then be embodied also for controlling the further operation of the computed tomography device, in particular, therefore, can also comprise an acquisition unit for recording computed tomography datasets, which acquisition unit can at least to some extent correspond to a provider unit for providing the computed tomography dataset.

The control device can comprise at least one processor and at least one storage device and have functional units formed from hardware and/or software for performing steps of the method according to one or more example embodiments of the present invention.

In particular, it can be provided that the control device comprises:
- a provider unit for providing a computed tomography dataset,
- a segmentation unit for segmenting at least one vascular tree supplying at least a part of the hollow organ in the computed tomography dataset, which unit may in addition be embodied also to perform an at least local segmentation of the hollow organ, as described,
- a determination unit for determining a two-dimensionally representable tree structure from the blood vessel segmentation result up to an order possible on the basis of the blood vessel segmentation result, wherein branches form nodes and blood vessel segments of an order form edges,
- an assignment unit for assigning, for each edge in the tree structure, perfusion information as the computed tomography data assigned to the blood vessel segment and/or at least one value derived therefrom,
- a definition unit for defining adjacent hollow organ segments of the hollow organ based on the supply by adjacent blood vessels in the tree structure,
- an analysis unit for analyzing the tree structure and the perfusion information for paths from a root of the tree structure to an end edge and/or for all edges of an order for determining the hemodynamic information assignable to hollow organ segments, and
- a visualization unit for visualizing at least a part of the hemodynamic information in the computed tomography dataset and/or a visualization dataset derived therefrom.

The control device can of course also include further functional units for performing preferred further optional steps of the method according to one or more example embodiments of the present invention.

A computer program according to one or more example embodiments of the present invention can be loaded directly into a storage device of a control device of an evaluation device and has a program for performing the steps of a method according to one or more example embodiments of the present invention when the computer program is executed on the control device. The computer program can be stored on an electronically readable data medium according to one or more example embodiments of the present invention, which therefore comprises control information comprising at least one computer program according to one or more example embodiments of the present invention and embodied in such a way that when the data medium is used in a control device of an evaluation device, the latter performs the steps of a method according to one or more example embodiments of the present invention. The data medium can be in particular a non-transitory data medium, a CD-ROM for example.

BRIEF DESCRIPTION OF THE DRAWINGS

Further advantages and details of the present invention will become apparent from the exemplary embodiments described below, as well as with reference to the drawings, in which.

DETAILED DESCRIPTION

Figure 1:
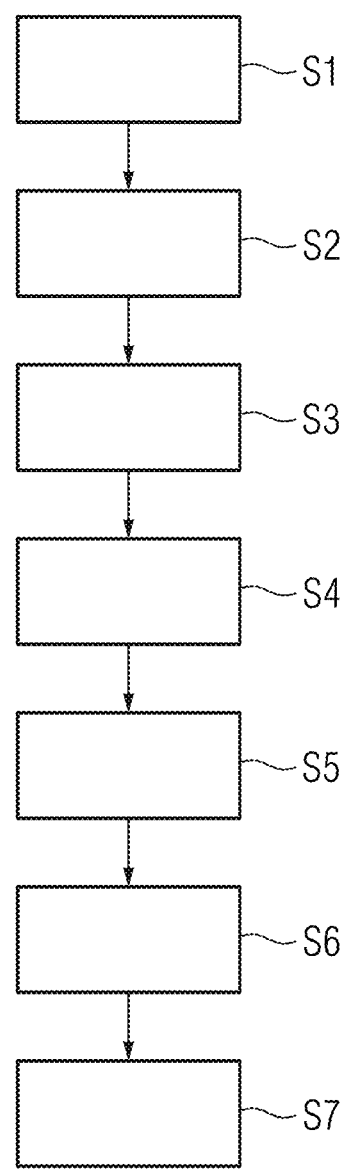
FIG. 1 shows a flowchart of an exemplary embodiment of the method according to the present invention.

FIG. 1 shows a flowchart of an exemplary embodiment of the method according to the present invention. First, in a step S1, an angiographic three-dimensional computed tomography dataset of a patient is provided in this case. The computed tomography dataset shows an acquisition region of the patient comprising a hollow organ, in this exemplary embodiment the intestine. The computed tomography dataset can be provided immediately, for example by its acquisition on a computed tomography device, but can also be retrieved from a storage device or system, for example a PACS.

Figure 2:
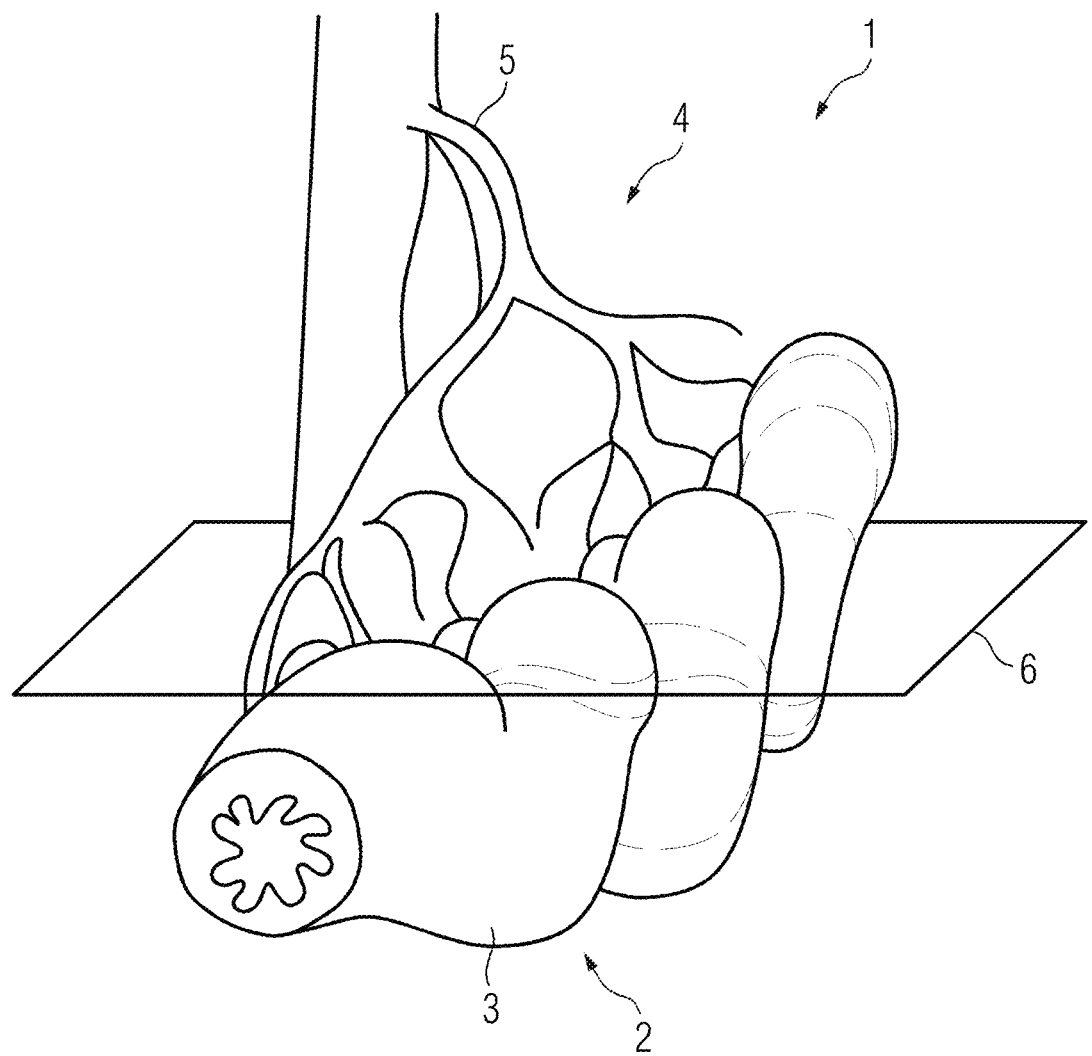
FIG. 2 shows a schematic view of an acquisition region containing a hollow organ and the vascular tree supplying it.

FIG. 2 shows an example of such an acquisition region 1, which in the present case comprises, as a hollow organ 2, the intestine 3, in particular the small intestine, of the patient, wherein the vascular tree 4 supplying the section of the intestine 3 illustrated here can also be clearly seen, starting for example from a mesenteric artery 5, since a contrast agent, in this case an iodinated contrast agent, has been administered to the patient. Evidently, the course of the blood vessels or blood vessel segments, just like that of the intestine 3, is extremely unclear. Were a visual, manual assessment of the computed tomography dataset to be carried out on the basis of sectional images through sectional planes 6, as often performed in the prior art, it would scarcely be possible to make an assignment of which courses are actually present. This makes the manual interpretation and evaluation of such computed tomography datasets very difficult, in particular when it is necessary to localize pathologies with maximum precision.

This is where the method according to one or more example embodiments of the present invention providing fully automatic support offers a solution. To that end, in a step S2, the vascular tree 4 is initially segmented in a first segmentation process. Since the computed tomography dataset in the present example is the result of a multi-energy imaging procedure, i.e. computed tomography data for different energy spectra is present, this can be used already within the scope of the segmentation in that a material decomposition takes place, for example a contrast agent dataset also quantitatively indicating the contrast agent concentration is calculated and referred to as the basis of the segmentation of the vascular tree 4. If a sufficiently robust method for segmentation of the hollow organ 2 is available, this also can be segmented already in step S2. The hollow organ 2, in this case the intestine 3, can be segmented for example on the basis of a fatty tissue layer surrounding it, in which case, however, the advantages of multi-energy imaging can also be called upon here. Further information can also be referred to for the segmentation of the hollow organ 2, for example a segmentation in a preliminary dataset which is registered with the computed tomography dataset, or the like. The computed tomography dataset itself can also be acquired in such a way that the segmentation of the hollow organ 2 is simplified, for example using a multi-contrast method. Segmentation algorithms generally known in the prior art can be called upon, in particular with regard to the vascular tree 4.

Figure 3:
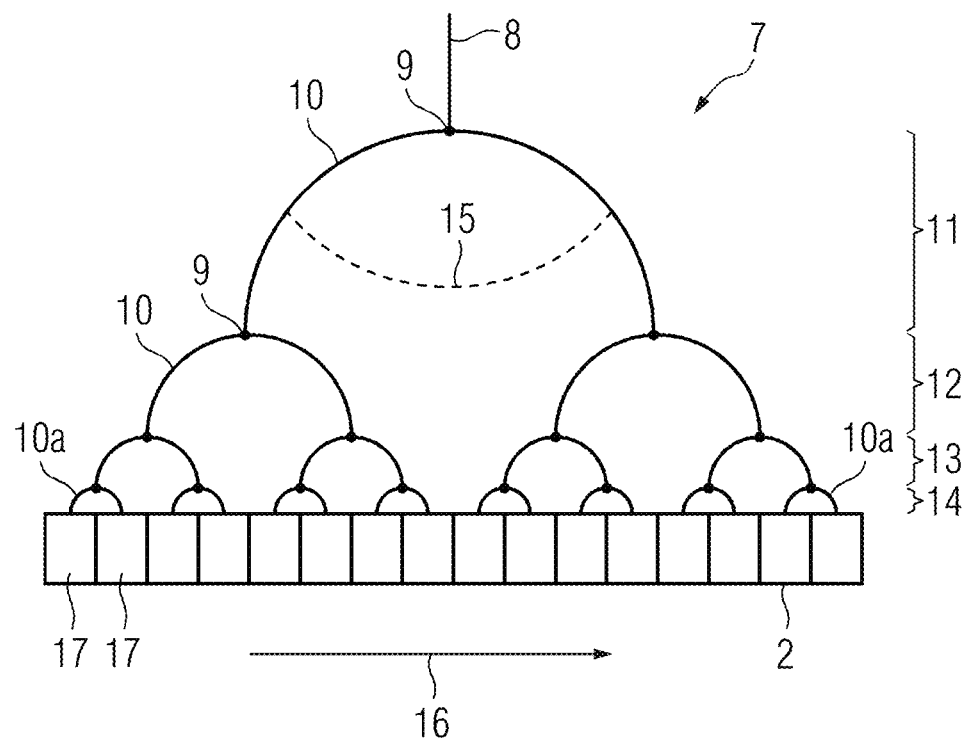
FIG. 3 shows a tree structure.

In a step S3, the blood vessel segmentation result is used in order to determine a tree structure 7 that can be represented in particular two-dimensionally in a visualization plane, cf. FIG. 3. In the tree structure 7, the mesenteric artery 5, the root 8 and each branch forms a node 9. The blood vessel segments lying between the branches or adjoining these form edges 10. The tree structure is continued over different orders 11, 12, 13, 14 insofar as the resolution permits, i.e. individual blood vessel segments can be distinguished. In the highest order 14, there are therefore end edges 10a present which correspond to blood vessel segments of which it is assumed that they supply certain hollow organ segments of the hollow organ 2.

The determining of the tree structure can be understood as a kind of blood vessel unfolding and projection onto a visualization plane.

In step S3, the regular structure of the blood supply of the hollow organ is then further exploited in order to determine thus far undetected blood vessel segments. For this purpose, a regularity of the tree structure 7 is assumed, with deviations from the regularity being determined as indicating missing blood vessel segments. If, for example, branches that were present in the other orders are missing in an order 11, 12, 13, 14, unsupplied blood vessel segments are to be assumed. These are then added to the tree structure 7 together with perfusion information indicating no flow, in which case it is also conceivable to attempt a further segmentation locally in order to locate these determined blood vessel segments, for example using a parameterization employing lower threshold values than in step S2. Perfusion information can then be determined also from the computed tomography data if necessary.

In this case, already in step S3 according to FIG. 1, collaterals are also detected which connect blood vessel segments outside of the order described here, and which are not taken into account for the tree structure 7 but are assigned as supplementary information 15 together with their attachment points of the tree structure 7.

In a step S4, perfusion information is then assigned to each edge 10, 10a in the tree structure 7. This can be formed by all the computed tomography data assigned to the respective blood vessel segment, though preferably it is formed by at least one value derived therefrom. Since in the present case an evaluation with regard to the blood flow or the hemodynamics generally is to be conducted, the already mentioned contrast agent dataset is used in the present case in order to be able to assign representative contrast agent concentrations as perfusion information to each edge 10, 10a. For example, a representative mean value or another statistical value, for example a summation, a median or the like can be used; it is also possible to use a plurality of such values, comprising in particular also variances or the like. Properties of the blood vessel segment that are derivable from the blood vessel segmentation result, for example the cross-section, can also be taken into consideration. If the computed tomography dataset comprises a plurality of computed tomography images acquired at different, in particular sequential time points, as a time series, time variation curves are determined in the present case for each value of the perfusion information and assigned to the respective edges 10, 10a. It is also possible to consider temporal mean values or to include properties of the time variation curve as values in the perfusion information. Statements relating to blood vessel segments determined as missing have already been made above.

A notional unfolding is also performed with regard to the hollow organ 2 in that this is regarded schematically as a sequence of hollow organ segments 17 extending along a hollow organ axis 16. In the present example, each end edge 10a, including end edges 10a added on account of blood vessel segments determined as missing, is assigned a hollow organ segment 17. Since the location of the blood vessel segments assigned to the end edges 10a is known from the blood vessel segmentation result, organ portions in the computed tomography dataset can also be assigned to the hollow organ segments 17 in step S5 in addition to the definition of the hollow organ segments 17. It is conceivable in this case also to estimate further undetected blood vessel segments besides and add them to the tree structure 7 since finally it can be checked whether regions assumable as belonging to the hollow organ 2 in the computed tomography dataset can be assumed as not supplied from the blood vessel segmentation result and/or organ portions are not assigned or, as the case may be, overly large organ portions would have to be assigned for hollow organ segments 17. Spacings between blood vessel segments of the end edges 10a, in particular along the at least locally segmented hollow organ 2, can also be analyzed in the process. Hollow organ portions, if present, can be specified according to the hollow organ segmentation result of step S2. An at least local segmentation is conceivable in any case. The organ portions can be chosen via a predefined or determinable environment around the position of the blood vessel segments assigned to the end edges 10a according to the blood vessel segmentation result, in particular limited to the hollow organ 2 according to an in particular local segmentation.

Figure 4:
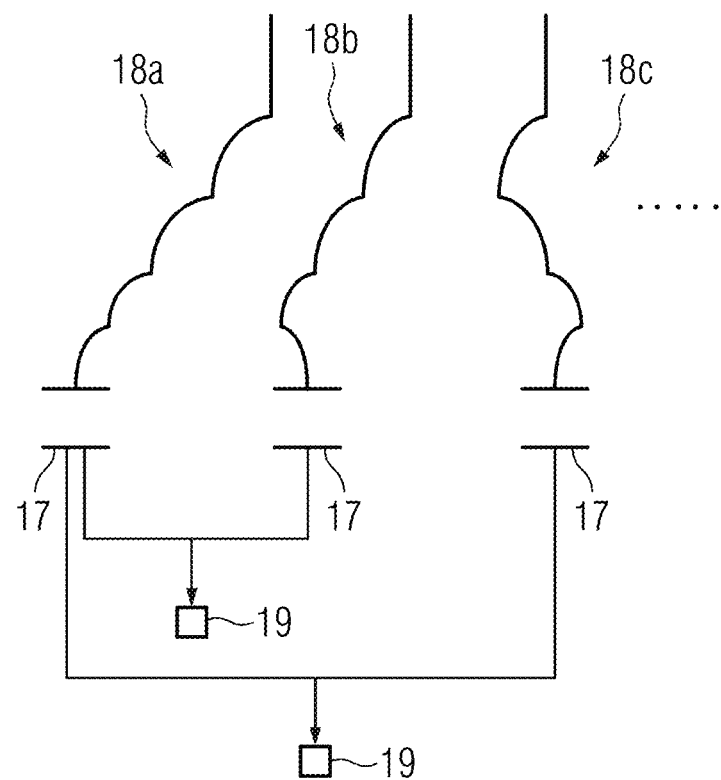
FIG. 4 shows paths in the tree structure and the assignment to hollow organ segments.

In a step S6, the analysis for determining hemodynamic information is then conducted. To that end, it can first be stated as a preliminary remark that, as shown in FIG. 4, a single, clearly defined path leads out from the root 8 to each end edge 10a (due to collaterals/cross-connections being disregarded). Three of these paths 18a, 18b and 18c through the tree structure 7 are shown by way of example in FIG. 4. Each of these paths ends at a hollow organ segment 17. In the present case, all possible paths 18 are considered, as indicated by the series of dots. In preparation for the analysis, pairs of paths 18 can now be assigned correlation values, indicated by the boxes 19, which finally describe the correlation of the bloodstream and later may help in assigning information to common phenomena, in differentiating phenomena and/or in distinguishing systemic effects from localized effects. In the present example, the paths 18a and 18b, which differ only in respect of the end edge 10a, display a significantly higher correlation than the paths 18a and 18c, for example. In this determination of correlation values, supplementary information 15 in respect of the collaterals is also taken into account since closer relationships can be restored via these.

In further preparation for the actual analysis, use is made of the fact that the hollow organ segments 17 are of course assigned organ portions in the computed tomography dataset, i.e. perfusion information can also be determined for these organ portions and consequently for the hollow organ segments 17, in this case once again using the contrast agent dataset. Thus, individual blood vessels and blood vessel segments may no longer be distinguishable in the tissue of the organ portions, yet the contrast agent present therein unquestionably indicates a strength of the perfusion. In the present example, the corresponding perfusion information is finally simply "attached" to the end edges 10a in the tree structure 7.

It should be noted that for undetected blood vessel segments of end edges 10a, determined for example on the basis of a deviation from the regularity of the tree structure, there of course exists no exact spatial assignment in the computed tomography dataset (unless the post-segmentation was successful), although owing to the positional information relating to the edges 10, 10a describing detected nearest-neighbor blood vessel segments, these can be estimated. In particular if an at least local segmentation of the hollow organ 2 is present, it is then very well possible to complete an assignment of hollow organ portions and to determine the perfusion information.

Figure 5:
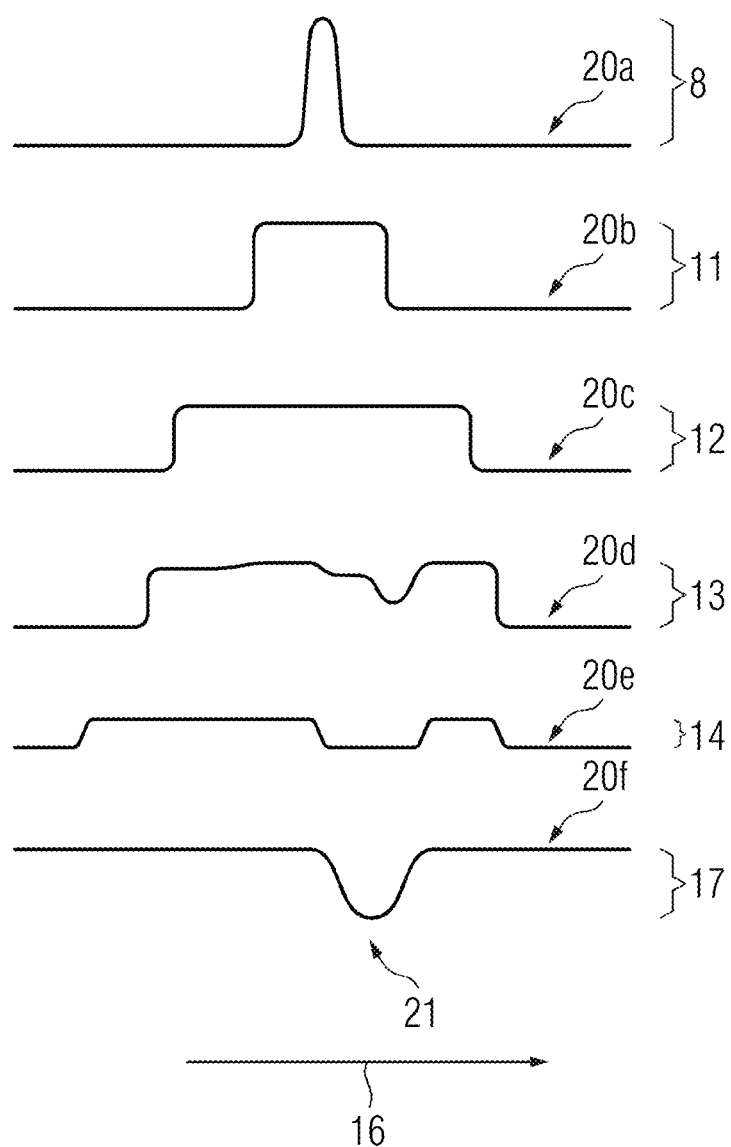
FIG. 5 shows first perfusion information curves, FIG. 6 schematically shows perfusion information present as time variation curves.

The actual analysis is now carried out on the one hand along the central-to-peripheral direction of the paths 18, and on the other hand, as is to be explained initially, also transversely on the planes of the different orders 11, 12, 13, 14. In this process, first perfusion information curves are determined in the different orders 11, 12, 13, 14 as well as for the hollow organ segments 17, i.e. along the notional hollow organ axis 16. Exemplary first perfusion information curves 20a-20f are shown in FIG. 5 for the case of an ischemia of the small intestine in a region 21, in this case a representative value, for example a mean value, of the contrast agent concentration having been drawn upon as perfusion information. As can be seen, blood is supplied through the mesenteric artery 5, corresponding to the root 8. The curves 20 then become visibly wider with the increasing number of blood vessel segments per order 11, 12, 13, 14. As of order 13, cf. the first perfusion information curve 20d, a dip occurs which continues in the first perfusion information curves 20e and 20f. In other words, the contrast agent concentrations for certain edges 10, 10a or hollow organ segments 17 diverge there significantly downward from those of the remaining edges 10, 10a or hollow organ segments 17, which is indicative of a hypoperfusion, i.e. the ischemia that is present. An upward deviation would indicate e hyperperfusion.

Figure 6:
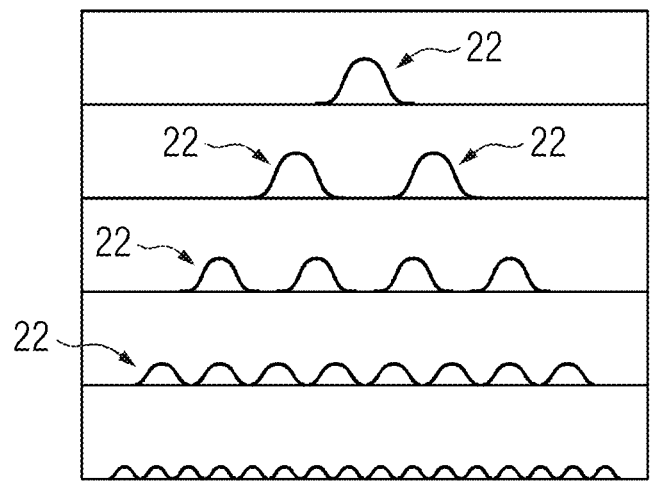

FIG. 6 shows purely schematically that, as already explained, time variation curves 22 may also be present in the case of a time series of computed tomography images instead of individual values in the perfusion information. In that case it is conceivable, for example, to use mean values of the fill phase or the like.

Figure 7:
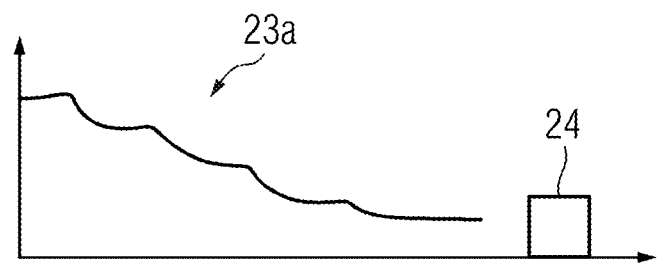
FIG. 7 shows a first example of a second perfusion information curve.
Figure 8:
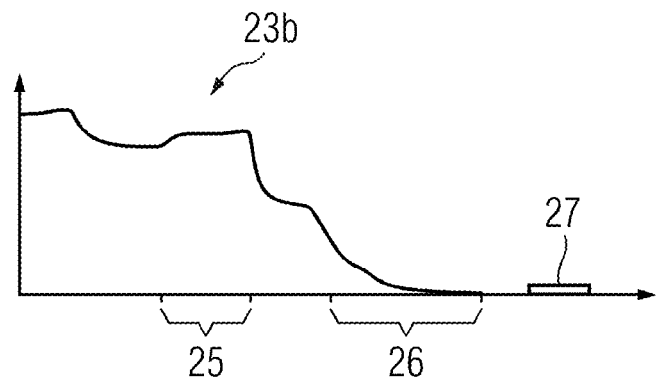
FIG. 8 shows a second example of a second perfusion information curve.

Second perfusion information curves are determined along the paths 18 from central to peripheral (i.e. root 8 to end edge 10a), exemplary second perfusion information curves 23a, 23b being shown in FIGS. 7 and 8. The second perfusion information curve 23a is a normal curve. As can be seen, increasingly less blood is transported due to the reduced blood vessel segment dimension, a certain value 24 also being given for the hollow organ segment 17.

However, the second perfusion information curve 23b shown in FIG. 8 is noteworthy in two respects. Firstly, a rise occurs once again in a section 25, which is indicative of the merging of a collateral. If this was not already identified anyway in step S3 and formulated as supplementary information 15, a corresponding piece of supplementary information 15 can now be added; if the collateral was already entered anyway, a plausibility check can be carried out.

Secondly, however, the second perfusion information curve 23b also drops away sharply toward the end edge 10a in a section 26, such that hardly any to no perfusion is present there, which is also indicated by the low value 27 for the assigned hollow organ segment 17. Clearly, a hypoperfusion, in particular also an ischemia, is present.

The deviation of the second perfusion information curve 23b can be confirmed by comparison of the second perfusion information curves 23 with one another and in particular by statistical consideration; as in the case of the first perfusion information curves 20 incidentally, however, a comparison with reference or comparison curves or values is conceivable.

In this exemplary embodiment, the second perfusion information curves 23 are used in step S6 also in order to determine hemodynamic parameters as part of the hemodynamic information, in particular based on consideration of the gradients and/or taking into account a respective vessel cross-section or vessel diameter of the blood vessel segments that can be derived from the blood vessel segmentation result. Particularly preferably, surrogate parameters for the perfusion, the blood flow and the blood flow reserve can be determined in this way, in particular also for the FFR. This results in particular in multiparametric maps which can also be used as a basis for further evaluations. It is furthermore possible, if hemodynamic parameters are determined for individual blood vessel segments, ultimately therefore edges 10, 10a, to correlate these with a reference, for example in the root 8 or, as the case may be, the mesenteric artery 5.

Such a further evaluation can be conducted for example in addition in step 7, cf. FIG. 1, which serves at least for the visualization of the hemodynamic information.

Figure 9:
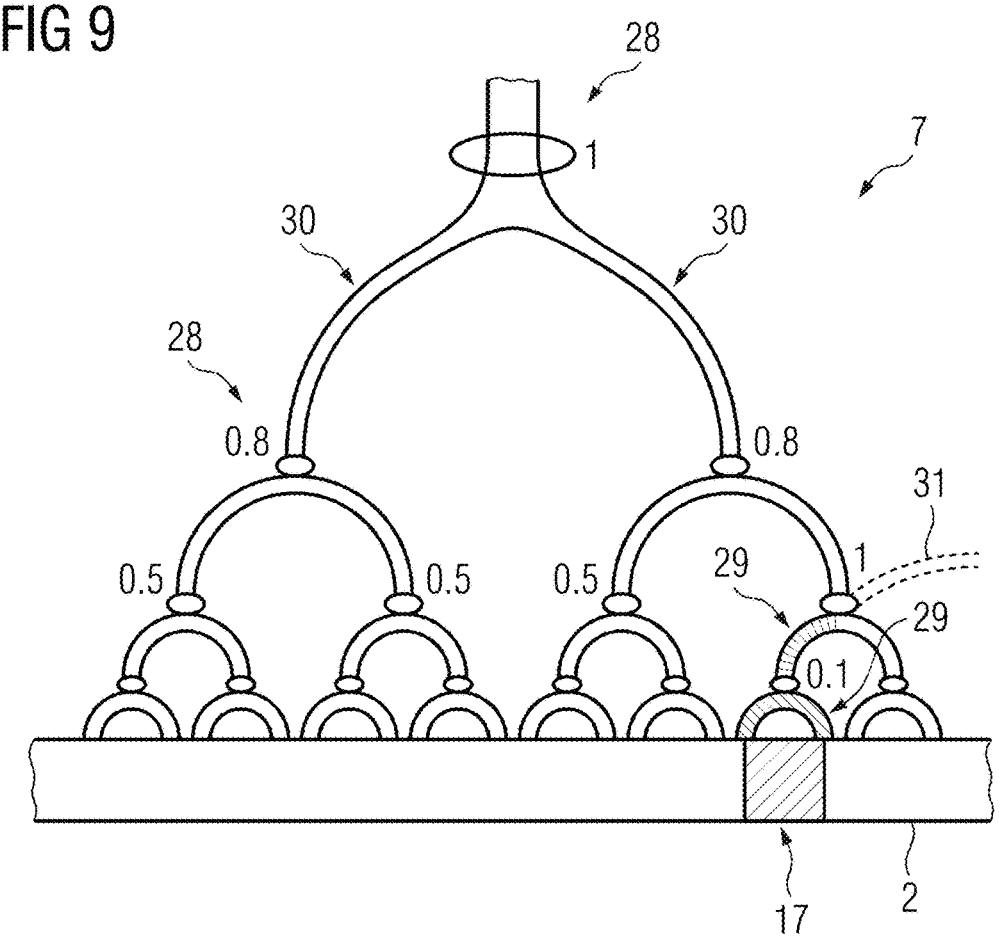
FIG. 9 shows a possible visualization of the tree structure including hemodynamic information.

FIG. 9 shows a first visualization option in the form of a visualization dataset schematically reproducing the tree structure 7 in the visualization plane and supplemented by hemodynamic information 28. As can be seen, schematically indicated blood vessel segments 29, which are poorly perfused, are highlighted in comparison with other schematically illustrated blood vessel segments 30. The unfolded hollow organ 2 is also shown schematically, together with correspondingly marked hollow organ segments 17. Collaterals 31 can also be indicated.

Figure 10:
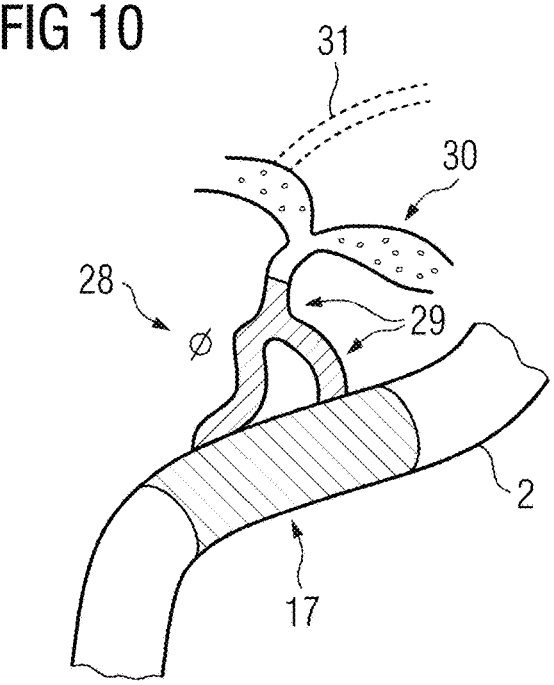
FIG. 10 shows a visualization of the computed tomography dataset including hemodynamic information.

FIG. 10 shows an overlay representation of hemodynamic information 28 over the schematically indicated computed tomography dataset, which in this case also shows the hollow organ 2 and blood vessel segments 29, 30, which are accordingly marked differently. This also applies to hollow organ segments 17 or, in this case, the corresponding organ portions. Colors can be used for example as a manner of highlighting or for differentiation.

In addition to the visualization options indicated here, it is of course also possible to choose other visualization options, for example cinematic overflight views of paths 18 or curved MPR views along their centerline that is derivable from the blood vessel segmentation result.

In this regard it should also be noted that anatomical landmarks can also be localized in step S2 and highlighted in the visualization, wherein anatomical landmarks can also be branches.

Figure 11:
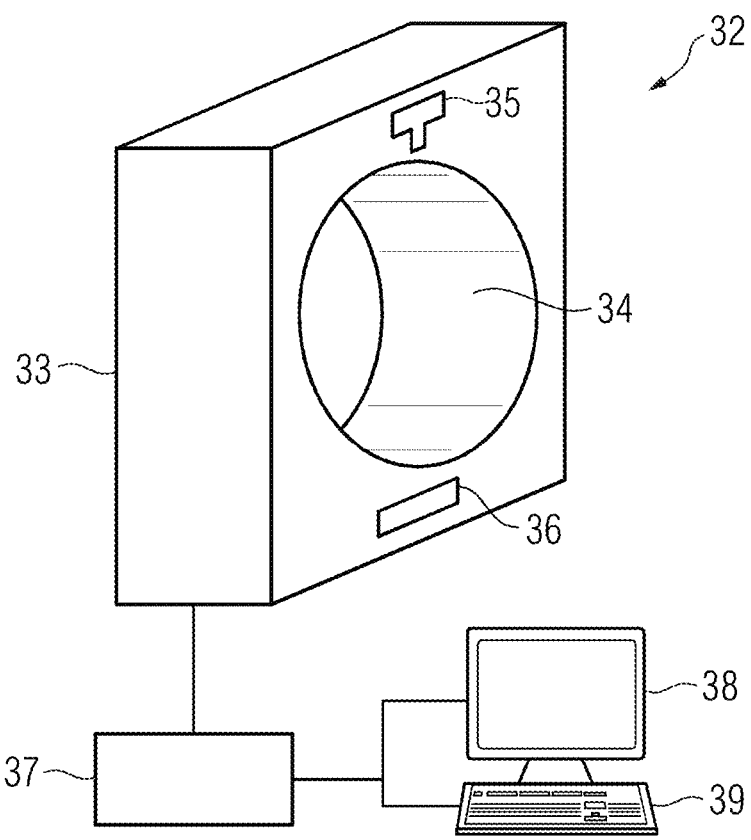
FIG. 11 shows a computed tomography device.

FIG. 11 shows a computed tomography device 32, also embodied as an evaluation device according to one or more example embodiments of the present invention, which, as is generally known, comprises a gantry 33 having a patient bore 34 into which the acquisition region of a patient can be introduced via a motorized patient couch (not shown in further detail here). A scanning arrangement comprising an X-ray source 35 and an X-ray detector 36, in this instance a photon-counting detector for multi-energy imaging, is rotatably mounted in the gantry 33. The operation of the computed tomography device 32 is controlled via a control device 37, to which a display device 38, for example a monitor, on which the visualization can take place, and an input device 39, for example for selecting a region of interest, are assigned.

Figure 12:
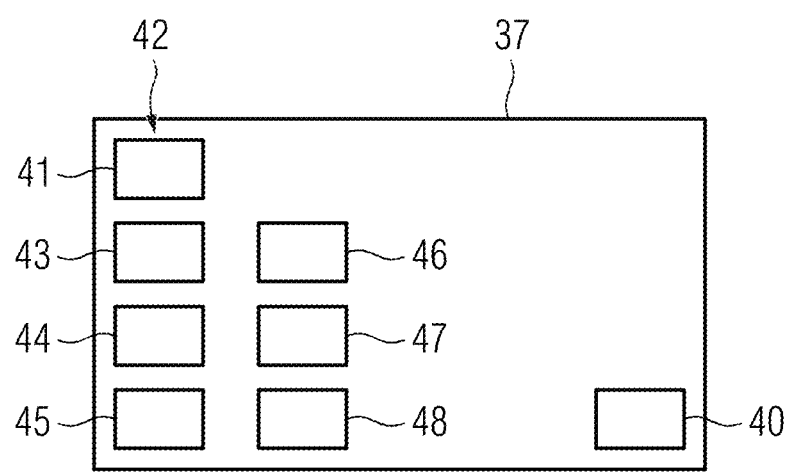
FIG. 12 shows the functional structure of a control device of the computed tomography device.

FIG. 12 shows the functional layout of the control device 37 in more detail. This comprises firstly a storage device 40 for temporary or longer-term storage of the computed tomography dataset, the hemodynamic information and intermediate results of the method. An acquisition unit 41 controls the scanning and reconstruction operation of the computed tomography device 32 and therefore acts in the present case as a provider unit 42 which provides the computed tomography dataset according to step S1. In the case of evaluation devices not embodied as a computed tomography device or integrated in the latter, the provider unit 42 can also be an interface accessing a storage device or system, in particular of a picture archiving system (PACS).

The segmentations according to step S2 in FIG. 1 are carried out in a segmentation unit 43. The tree structure 7 is determined according to step S3 in a determination unit 44, and the perfusion information is assigned to the edges 10, 10a in an assignment unit 45 (cf. step S4). The control device 37 further comprises a definition unit 46, which defines not only the hollow organ segments 17, but, as described with reference to step S5, also assigns the associated organ portions in the computed tomography dataset.

The hemodynamic information is determined as described with reference to step S6 in an analysis unit 47, after which a visualization unit 48 can be used in order to visualize the hemodynamic information according to step S7, for example using the display device 38.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in more detail on the basis of a preferred exemplary embodiment, the present invention is not limited by the disclosed examples and other variations can be derived herefrom by the person skilled in the art without leaving the scope of protection of the present invention.

What is claimed is:

1. A computer-implemented method for evaluating an angiographic three-dimensional computed tomography dataset of an acquisition region including a hollow organ of a patient, wherein at least one piece of spatially resolved hemodynamic information with respect to the hollow organ is determined, and wherein the method comprises:
   providing the computed tomography dataset;
   segmenting at least one vascular tree supplying at least a part of the hollow organ in the computed tomography dataset;
   determining, from a blood vessel segmentation result, a two-dimensionally representable tree structure up to an order possible based on the blood vessel segmentation result, wherein branches form nodes and blood vessel segments of an order form edges;
   assigning perfusion information for each edge in the two-dimensionally representable tree structure as at least one of computed tomography data assigned to the blood vessel segment or at least one value derived therefrom;
   defining adjacent hollow organ segments of the hollow organ based on supply by adjacent blood vessels in the two-dimensionally representable tree structure;
   analyzing the two-dimensionally representable tree structure and the perfusion information for paths from a root of the two-dimensionally representable tree structure to at least one of an end edge or for all edges of an order to determine hemodynamic information to assign to hollow organ segments; and
   visualizing at least a part of the hemodynamic information in at least one of the computed tomography dataset or a visualization dataset derived therefrom.

2. The computer-implemented method as claimed in claim 1, wherein
   in case of a computed tomography dataset acquired using multi-energy imaging, a contrast agent dataset obtained by material decomposition is used for at least one of segmenting the at least one vascular tree or determining at least a part of the perfusion information.

3. The computer-implemented method as claimed in claim 2, further comprising:
   determining missing blood vessel segments not detected during blood vessel segmentation by evaluating the two-dimensionally representable tree structure assuming a regularity of the two-dimensionally representable tree structure, wherein deviations from the regularity are determined as indicating the missing blood vessel segments.

4. The computer-implemented method as claimed in claim 1, further comprising:
   determining missing blood vessel segments not detected during blood vessel segmentation by evaluating the two-dimensionally representable tree structure assuming a regularity of the two-dimensionally representable tree structure, wherein deviations from the regularity are determined as indicating the missing blood vessel segments.

5. The computer-implemented method as claimed in claim 4, further comprising at least one of:
adding the missing blood vessel segments of the two-dimensionally representable tree structure based on a location in the two-dimensionally representable tree structure, or
performing a further blood vessel segmentation process for an evaluation region in the computed tomography dataset to find the missing blood vessel segments.

6. The computer-implemented method of claim 5, wherein the further blood vessel segmentation process is based on a changed parameterization.

7. The computer-implemented method as claimed in claim 1, further comprising:
assigning organ portions in the computed tomography dataset to hollow organ segments based on position information of the blood vessel segments of end edges known from the blood vessel segmentation result, the hollow organ segments defined based on the two-dimensionally representable tree structure.

8. The computer-implemented method as claimed in claim 7, wherein at least one of
the organ portions are specified at least one of
based on at least one of a predefined environment or an environment determined based on positional information of adjacent blood vessel segments, or
based on a segmentation of the hollow organ, or
the organ portions are highlighted at least partially in the visualizing.

9. The computer-implemented method as claimed in claim 7, further comprising:
determining perfusion information from computed tomography data of an organ portion for each hollow organ segment assigned to an end edge; and
at least one of inserting said perfusion information into the two-dimensionally representable tree structure or assigning said perfusion information to the respective end edge.

10. The computer-implemented method as claimed in claim 1, further comprising:
removing, from the two-dimensionally representable tree structure, at least one of collaterals or anastomoses detected during at least one of the determining of the two-dimensionally representable tree structure or the analyzing of the perfusion information; and
storing the at least one of the collaterals or anastomoses together with their attachment points as supplementary information to the two-dimensionally representable tree structure, wherein
the supplementary information is taken into account at least one of in determining the hemodynamic information or in the visualizing.

11. The computer-implemented method as claimed in claim 1, wherein for analyzing the perfusion information for at least one order, the method comprises:
determining a first perfusion information curve over all blood vessel segments of the order; and
analyzing the first perfusion information curve to determine the hemodynamic information.

12. The computer-implemented method as claimed in claim 11, wherein in case of a deviation fulfilling a relevance criterion of a piece of perfusion information from a plurality of the perfusion information of the first perfusion information curve or a predefined, order-specific comparison value in a blood vessel segment, a hyperperfusion is determined in case of an upward deviation, and a hypoperfusion in case of a downward deviation.

13. The computer-implemented method of claim 11, wherein the analyzing the first perfusion information curve includes statistically analyzing the first perfusion information curve to determine the hemodynamic information.

14. The computer-implemented method as claimed in claim 1, wherein for at least a path among the paths from a root of the two-dimensionally representable tree structure to an end edge, the method comprises:
determining a second perfusion information curve over all blood vessel segments of the path; and
analyzing the second perfusion information curve to determine the hemodynamic information.

15. The computer-implemented method as claimed in claim 14, wherein
the analyzing the second perfusion information curve is conducted by at least one of comparison of second perfusion information curves assigned to different paths or comparisons with at least one reference value for at least one gradient in order to determine at least one of a hyperperfusion, a hypoperfusion, or that at least one of a collateral or an anastomosis is indicated in the event of a positive gradient in a peripheral direction.

16. The computer-implemented method of claim 14, wherein the analyzing the second perfusion information curve comprises:
analyzing the second perfusion information curve with respect to a gradient.

17. The computer-implemented method as claimed in claim 15, wherein the hemodynamic information includes at least one hemodynamic parameter.

18. The computer-implemented method of claim 15, wherein the comparison of second perfusion information curves assigned to different paths includes a statistical comparison.

19. The computer-implemented method as claimed in claim 17, wherein a surrogate parameter for at least one of perfusion, blood flow or a blood flow reserve is determined as the hemodynamic parameter, taking into account at least one of a vessel diameter that is derivable from the blood vessel segmentation result or an influence of at least one of collaterals or anastomoses.

20. The computer-implemented method of claim 19, wherein the blood flow reserve is a Fractional Flow Reserve.

21. The computer-implemented method as claimed in claim 1, further comprising:
determining, for at least one pair of paths from a root of the two-dimensionally representable tree structure to an end edge, a correlation value describing a common blood supply taking into account collaterals and anastomoses, wherein
the correlation value is usable for assigning comparable hemodynamic behaviors to common behavioral regions.

22. The computer-implemented method as claimed in claim 1, wherein, for visualization purposes,
realizing at least one of a cinematic vessel representation, an overlay representation of hemodynamic information, or a highlighting of at least one of hollow organ segments or blood vessel segments resulting as a function of hemodynamic information, or
determining, as the visualization dataset, a curved MPR along at least one vessel centerline determined from the blood vessel segmentation result.

23. The computer-implemented method of claim 1, wherein the hollow organ is an intestine.

24. An evaluation device to evaluate an angiographic three-dimensional computed tomography dataset of an acquisition region including a hollow organ of a patient, wherein at least one piece of spatially resolved hemodynamic information with respect to the hollow organ is determined, and wherein the evaluation device comprises:
- a control device including at least one processor and a memory, the memory configured to store computer-readable instructions, and the processor configured to execute the computer-readable instructions to cause the control device to
- segment at least one vascular tree supplying at least a part of the hollow organ in the computed tomography dataset,
- determine, from a blood vessel segmentation result, a two-dimensionally representable tree structure up to an order possible based on the blood vessel segmentation result, wherein branches form nodes and blood vessel segments of an order form edges,
- assign perfusion information for each edge in the two-dimensionally representable tree structure as at least one of computed tomography data assigned to the blood vessel segment or at least one value derived therefrom,
- define adjacent hollow organ segments of the hollow organ based on supply by adjacent blood vessels in the two-dimensionally representable tree structure,
- analyze the two-dimensionally representable tree structure and the perfusion information for paths from a root of the two-dimensionally representable tree structure to at least one of an end edge or for all edges of an order to determine hemodynamic information to assign to hollow organ segments, and
- visualize at least a part of the hemodynamic information in at least one of the computed tomography dataset or a visualization dataset derived therefrom.

25. A non-transitory computer readable storage medium storing a computer program that, when executed on a control device of an evaluation device, causes the evaluation device to perform the method of claim 1.

* * * * *